(12) United States Patent
Ausubel et al.

(10) Patent No.: US 6,461,854 B1
(45) Date of Patent: Oct. 8, 2002

(54) METHODS OF SCREENING COMPOUNDS USEFUL FOR PREVENTION OF INFECTION OR PATHOGENICITY

(75) Inventors: Frederick M. Ausubel, Newton; Laurence G. Rahme, Brookline; Man-Wah Tan, Somerville; Gary B. Ruvkun, Cambridge, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/411,560

(22) Filed: Mar. 28, 1995

(51) Int. Cl.[7] .................. A61K 49/00; C12N 9/92; C12N 1/20

(52) U.S. Cl. .................. 435/252.3; 424/9.1; 424/234.1; 435/4; 435/42; 435/410; 435/243; 435/252.34

(58) Field of Search .................. 435/172.1, 172.3, 435/252.3, 252.34, 253.3, 4, 42, 410, 243; 935/23, 72, 76, 79, 80; 424/9.1, 234.1

(56) References Cited

U.S. PATENT DOCUMENTS

| | | | |
|---|---|---|---|
| 4,713,378 A | 12/1987 | Perrone et al. | |
| 5,270,448 A | 12/1993 | Payne | 530/350 |
| 5,366,995 A | 11/1994 | Savage et al. | |

FOREIGN PATENT DOCUMENTS

| | | |
|---|---|---|
| WO | WO 94/16077 | 7/1994 |
| WO | WO 95/11969 | 5/1995 |

OTHER PUBLICATIONS

Fenselau, S. et al. 1992. "Determinants of Pathogenicity in *Xanthomonas campestris* pv. vesicatoria are Related to Proteins Involved in Secretion in Bacterial Pathogens of Animals." *Molecular Plant–Microbe Interactions* 5(5):390–396.*
Xu, P. et al., 1988. "Molecular Cloning of Genes That Specify Virulence in *Pseudomonas solanacearum*." *Journal of Bacteriology* 170(2):617–622.*
Alexander et al., "Surgical Infections And Choice Of Antibiotics," In: Textbook of Surgery, Sabiston, D.C., (ed.), Saunders, W.B., Philadelphia, PA pp. 221–236 (1991).
Bent et al., "RPS2 of *Arabidopsis thaliane*: A Leucine–Rich Repeat Class of Plant Disease Resistance Genes," *Science* 265:1856–1860 (1994).
Berka et al., "Phospholipas C (Heat–Labile Hemolysin) of *Pseudomonas aeruginosa*: Purification and and Preliminary Characterization," *J.Bacteriology* 152:239–245 (1982).
Debener et al., "Identification and Molecular Mapping of a Single *Arabidopsis thaliana* Locus Determining Resistance to a Phytopathogenic *Pseudomonas syringae* Isolate," *The Plant Journal* 1:289–302 (1991).
Dong et al., "Induction of *Arabidopis* Defense Genes by Virulent and Avirulent *Pseudomonas syringae* Strains and by a Cloned Avirulence Gene," *The Plant Cell* 3:61–72 (1991).
Elrod et al., "*Pseudomonas aeruginosa*: Its Role As A Plant Pathogen," *J. Bacteriology* 46:633–645 (1942).
Green et al., "Agricultural Plants and Soil as a Reservoir for *Pseudomonas aeruginosa*," *Appl. Microbiology* 28:987–991 (1974).
Holloway, "Genetic recombination in *Pseudomonas aeruginosa*," *J. gen. Microbiol.* 13:572–581 (1955).
Huang et al., "The *Pseudomonas syringae* pv. syringae 61 hrpH Product, an Envelope Protein Required for Elicitation of the Hypersentive Response in Plants," *J. Bacteriology* 174:6878–6885 (1992).
Iglewski et al., "NAD–Dependent Inhibition of Protein Synthesis by *Pseudomonas aeruginosa* Toxin," *Proc. Nat. Acad. Sci. USA* 72:2284–2288 (1975).
Ishimoto et al., "Formation of Pilin in *Pseudomonas aeruginosa* Requires the Alternative σ Factor (RpoN) of RNA Polymerase," *Proc. Natl. Acad. Sci. USA* 86:1954–1957 (1989).
Kominos et al., "Introduction of *Pseudomonas aeruginosa* Into a Hospital via Vegetables," *Appl. Microbiol.* 24:567–570 (1972).
Kovalchik et al., "*Neisseria gonorrhoeae*: Colonial Morphology of Rectal Isolates," *Appl. Microbiology* 23:986–989 (1972).
Kunkel et al., "RPS2, an *Arabidopsis* Disease Resistane Locus Specifying Recognition of *Pseudomonas syringae* Strains Expressing the Avirulence Gene avrRpt2," *The Plant Cell* 5:865–875 (1993).
Laville et al., "Global Control in *Pseudomonas fluorescens* Mediating Antibiotic Synthesis and Suppression of Black Root Rot of Tobacco," *Proc. Natl. Acad. Sci. USA* 89:1562–1566 (1992).
Meyers et al., "Infections Caused by Microorganisms of the Genus *Erwinia*," *Annals of Internal Medicine* 76:9–14 (1972).
Ohman et al., "Toxin A–Deficient Mutants of *Pseudomonas aeruginosa* PA103: Isolation and Characterization," *Infection and Immunity* 28:899–908 (1980).
Ostroff et al., "Identification of a New Phospholipase C Activity by Analysis of an Insertional Mutation in the Hemolytic Phospholipase C Structural Gene of *Pseudomonas aeruginosa*," *J. Bacteriology* 169:4597–4601 (1987).

(List continued on next page.)

*Primary Examiner*—Rodney P Swartz
(74) *Attorney, Agent, or Firm*—Clark & Elbing LLP (57) ABSTRACT

Screening procedures are disclosed for identifying compounds useful for inhibiting infection or pathogenicity. Methods are also disclosed for identifying pathogenic virulence factors.

12 Claims, 4 Drawing Sheets

(1 of 4 Drawing Sheet(s) Filed in Color)

OTHER PUBLICATIONS

Rich et al., "Genetic Evidence that the gacA Gene Encodes the Cognate Response Regulator for the lemA Sensor in *Pseudomonas syringae*," *J. Bacteriology* 176:7468–7475 (1994).

Stevens et al., "A Quantitative Model of Invasive *Pseudomonas* Infection in Burn Injury," *J. Burn Care & Rehabilitation* 15:232–235 (1994).

Geels F.P., "*Pseudomonas tolaasii* control by kasugamycin in cultivated mushrooms (*Agaricus bisporus*)", *J.Applied Bacteriology* 79: 38–42, (1995).

Grewal P.S. and Hand P., "Effects of bacteria isolated form a *Saprophagous rhabditid nematode Caenorhabditis elegans* on the mycelial growth of *Agaricus bisporus*", *J. Applied Bacteriology*, 72: 173–179, (1992).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

GCTAGTAGTC GATGACC      17

(2) INFORMATION FOR SEQ ID NO:2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear -continued (ii) MOLECULE TYPE: DNA (genomic)

(xi) SEQUENCE DESCRIPTION: SEQ ID NO:2:

GCTGGCATCA ACCATGC                                            17

METHODS OF SCREENING COMPOUNDS USEFUL FOR PREVENTION OF INFECTION OR PATHOGENICITY

BACKGROUND OF THE INVENTION

The invention relates to screening procedures which identify compounds for inhibiting infection or disease in a eukaryotic host organism, or which induce or stimulate a host's pathogenic defense mechanisms. The invention also relates to the use of such compounds as anti-pathogens. In addition, the invention relates to procedures which identify pathogenic virulence factors.

Microbial pathogens such as bacteria, protozoa, fungi, nematodes, and viruses include a large and diverse group of organisms capable of infecting animals and plants. Initiation of an infection occurs when the infecting organism is pathogenic, and the host is susceptible to pathogenic invasion. After establishing contact with susceptible cells or tissues of the host, the pathogen acquires nutrients from its host, facilitating its own survival. During the infection process the pathogen activates a cascade of molecular, biochemical, and physiological processes, the result of which is the release of substances detrimental to the host and the development of disease (See, e.g., *Scientific American Medicine*, W.H. Freeman and Co., San Francisco, 1995; Agrios, G. N., Plant Pathology, Academic Press, 1988). The pathogenic effects of microbes are produced in a variety of ways.

Some pathogens act through secreted products. Diphtheria, for instance, is caused by the bacillus, *Cornynebacterium diptheriae*. This organism is inhaled by the host and establishes infection in the upper respiratory tract. While the bacterium does not itself invade the bloodstream, its powerful toxins do. These toxins are then absorbed by the cells of the body, enzyme function is impaired, and host cells are destroyed.

Other diseases are the result of the body's reaction to a pathogen. For example, in pneumonia, a disease caused by *Streptococcus pneumoniae*, infection causes an outpouring of fluid and cells into the air sacs of the lungs, interfering with respiration. Fungal infections of the skin similarly result from such inflammatory responses.

Yet other bacteria are opportunistic pathogens. *Pseudomonas aeruginosa*, for example, infects patients with thermal burns and patients who are immunodeficient or otherwise immunologically compromised. *P. aeruginosa* infections can be acute and localized as in corneal ulcers and otitis media, chronic as in the lungs of cystic fibrosis patients, or systemic following bloodstream invasion.

Plant pathogenic diseases are also of concern because they cause damage to plants and plant products. Phytopathogens produce disease in plants by any number of methods including: (1) consuming host cell nutrients; (2) killing or disrupting host cell metabolism through toxins, enzymes, or growth-regulators; (3) affecting photosynthesis by inducing chlorosis (e.g., by degrading chloroplasts); and (4) blocking conductive tissues and interfering with normal physiological processes.

Crop plants, ornamentals, trees, and shrubs are especially vulnerable to diseases caused by bacteria, fungi, viruses, and nematodes. Phytopathogenic bacteria, for example, cause the development of many disease symptoms including leaf spots and blights, soft-rots, wilts, overgrowths, scabs, and cankers. Bacterial diseases occur most commonly on vegetables (and some ornamentals) that have fleshy storage tissues, such as potatoes, carrots, onions, iris, or hyacinth. They may also occur in plants bearing fleshy fruit (such as cucumber, squash, eggplant, or tomato), as well as in leafy plants (such as cabbage, celery, lettuce, or spinach). Plant bacterial diseases occur throughout the world and cause serious damage to crops in the field, in transit, and in storage.

The mechanisms of plant pathogenesis are many and varied. One bacterial phytopathogen Erwinia, for example, causes plant diseases such as soft-rot and fire-blight by penetrating a plant through a wound or an accessible natural opening. Once inside, the bacteria secrete enzymes which break down the plant's middle lamellae, resulting in the maceration of tissue and ultimately cell death. Other bacteria, such as certain strains of Pseudomonas, may interfere with water translocation by disrupting xylem within the plant. Pseudomonads invade the xylem of roots and stems and, once inside, secrete enzymes and toxins which destroy the plant. Still other phytopathogenic bacteria, like Agrobacterium and Corynebacterium, stimulate cell division and cell enlargement in affected tissues. This generally leads to the development of amorphous overgrowths, galls, or tumors on roots, stems, or other organs (e.g., crown gall caused by *Agrobacterium tumefaciens*), or in the proliferation of infected organs (e.g., hairy root caused by *Agrobacterium rhizogenes*).

Prompt identification of the causative organism is essential to the appropriate selection of anti-pathogenic agents and successful management of clinical and agricultural infections. However, the extensive use of anti-pathogenic agents, such as sulfonamides, tetracyclines, ampicillins, cephalosporins, and aminoglycosides, in both medicine and agriculture has strongly favored the selection of resistant microbial species. This is especially true of bacterial strains containing transmissible resistance plasmids. For example, outbreaks of nosocomial infections from highly resistant strains of Serratia, Klebsiella, Pseudomonas, Acinetobacter, Enterobacter, and Streptococcus have become important and recurrent problems. As a result of selecting resistant strains, over the past few decades, *P. aeruginosa* has emerged as an important and problematic clinical pathogen, causing between 10% and 20% of infections in hospitals. Currently, several aminoglycosides and third-generation cephalosporins are efficacious against *P. aeruginosa*, but the relative ease with which *P. aeruginosa* acquires resistance necessitates the search for new compounds as potential replacements or alternative therapies.

SUMMARY OF THE INVENTION

We have discovered that common pathogenic virulence factors are involved in the infection and pathogenicity of both animal and plant hosts. The identification of such host-independent virulence factors has facilitated improved screening methods designed to evaluate and identify therapeutic agents useful for inhibiting pathogenesis in either animal or plant hosts, or both. Furthermore, our discovery provides the basis for screening methods useful for identifying a variety of new virulence factors. Identification of such virulence factors also facilitates the development of targeted reagents for use as anti-pathogens.

In a first aspect, therefore, the invention generally features a method for identifying a compound which is capable of inhibiting a pathogen in a eukaryotic host organism. The method involves (a) exposing (either sequentially or simultaneously) at least two different eukaryotic host organisms, at least one of the organisms being a non-rodent, to a single pathogen in the presence of at least one candidate compound; and (b) identifying a compound that inhibits the pathogen in each of the eukaryotic host organisms.

In preferred embodiments, the pathogen is a bacterium (e.g., *Pseudomonas aeruginosa* UCBPP-PA14); the eukaryotic host organisms include a vertebrate (e.g., a non-rodent) and a plant, a vertebrate and an invertebrate; or an invertebrate and a plant. Preferably, the invertebrate is a nematode (e.g., a member of the genus Caenorhabditis); and the plant is a crucifer (e.g., a member of the genus Arabidopsis). In other preferred embodiments, each of the eukaryotic host organisms is a plant; is a vertebrate; or is an invertebrate.

In a second aspect, the invention generally features a method for identifying a compound which is capable of inhibiting a pathogen in a non-rodent eukaryotic host organism. The method involves (a) exposing a non-rodent eukaryotic host organism to a single pathogen in the presence of at least one candidate compound; and (b) identifying a compound that inhibits the pathogen in the eukaryotic host organisms.

In one preferred embodiment, the pathogen is a bacterium (e.g., *Pseudomonas aeruginosa* UCBPP-PA14), and the non-rodent eukaryotic host organism is a nematode (e.g., a member of the genus Caenorhabditis), and the plant is a crucifer (e.g., is a member of the genus Arabidopsis). In a second preferred embodiment, the pathogen is a bacterium (e.g., *Pseudomonas aeruginosa* UCBPP-PA14), and the non-rodent eukaryotic host organism is a plant (e.g., is a member of the genus Arabidopsis).

In a third aspect, the invention generally features a method for identifying a pathogenic virulence factor. The method involves (a) identifying a pathogen which is capable of infecting at least two different eukaryotic host organisms, at least one of the organisms being a non-rodent; (b) generating a mutant of the pathogen; (c) exposing (either sequentially or simultaneously) each of the organisms to the mutated pathogen; (d) determining whether the mutated pathogen is capable of causing disease in each of the organisms, a reduction of disease in both of the organisms relative to that caused by the wild-type pathogen indicating a mutation in a pathogenic virulence factor; and (e) using the mutation as a marker for identifying the pathogenic virulence factor.

In a fourth aspect, the invention generally features a method for mutating a pathogenic virulence factor. The method involves: (a) identifying a pathogen which is capable of infecting at least two different eukaryotic host organisms, at least one of the organisms being a non-rodent; (b) generating a mutant of the pathogen; (c) exposing (either sequentially or simultaneously) each of the organisms to the mutated pathogen; and (d) determining whether the mutated pathogen is capable of causing disease in each of the organisms, a reduction of disease in both of the organisms relative to that caused by the wild-type pathogen indicating a mutation in a pathogenic virulence factor.

In a fifth aspect, the invention generally features a method of reducing the virulence of a pathogen. The method involves (a) identifying a pathogen which is capable of infecting at least two different eukaryotic host organisms, at least one of the organisms being a non-rodent; (b) generating a mutant of the pathogen; (c) exposing (either sequentially or simultaneously) each of the organisms to the mutated pathogen; and (d) determining whether the mutated pathogen is capable of causing disease in each of the organisms, a reduction of disease in both of the organisms relative to that caused by the wild-type pathogen indicating a reduction in pathogen virulence.

By "inhibiting a pathogen" is meant the ability of a candidate compound to decrease, suppress, attenuate, diminish, or arrest the development or progression of a pathogen-mediated disease or an infection in a eukaryotic host organism. Preferably, such inhibition decreases pathogenicity by at least 5%, more preferably by at least 25%, and most preferably by at least 50%, as compared to symptoms in the absence of candidate compound in any appropriate pathogenicity assay (for example, those assays described herein). In one particular example, inhibition may be measured by monitoring pathogenic symptoms in a host organism exposed to a test compound or extract, a decrease in the level of symptoms relative to the level of pathogenic symptoms in a host organism not exposed to the compound indicating compound-mediated inhibition of the pathogen.

By "non-rodent" is meant any organism that is not a mouse, a rat, a guinea pig, or a hamster.

By "pathogenic virulence factor" is meant a cellular component (e.g., a protein such as a transcription factor) without which the pathogen is incapable of causing disease or infection in a eukaryotic host organism.

The invention provides long awaited advantages over a wide variety of standard screening methods used for distinguishing and evaluating the efficacy of a compound against microbial pathogens. For example, the screening methods described herein allow for the simultaneous evaluation of host toxicity as well as anti-pathogen potency in a simple in vivo screen. Moreover, the methods of the invention allow one to evaluate the ability of a compound to inhibit microbial pathogenesis, and, at the same time, to evaluate the ability of the compound to stimulate and strengthen a host's response to pathogenic attack.

Accordingly, the methods of the invention provide a facile means to identify compounds that are safe for use in eukaryotic host organisms (i.e., compounds which do not adversely affect the normal development and physiology of the organism), and efficacious against pathogenic microbes (i.e., by suppressing the virulence of a pathogen). In addition, the methods of the invention provide a route for analyzing virtually any number of compounds for anti-pathogenic effect with high-volume throughput, high sensitivity, and low complexity. The methods are also relatively inexpensive to perform and enable the analysis of small quantities of active substances found in either purified or crude extract form. Furthermore, the methods disclosed herein provide a means for identifying anti-pathogenic compounds which have the capability of crossing eukaryotic cell membranes and which maintain therapeutic efficacy in an in vivo method of administration.

Other features and advantages of the invention will be apparent from the following description of the preferred embodiments thereof, and from the claims.

DETAILED DESCRIPTION

The drawings will first be described.

Drawings

The patent file contains one drawing executed in color. Copies of this patent with the color drawing will be provided by the Patent and Trademark Office upon request and payment of the necessary fee.

FIGS. 2A–D are graphs showing the growth of *Pseudomonas syringae* and *Pseudomonas aeruginosa* in Arabidopsis leaves.

Below we describe experimental evidence demonstrating that a bacterial pathogen is capable of causing disease in both a plant, in an animal, and in a nematode, and that there is an overlap in virulence factors responsible for causing microbial pathogenic disease in plants, animals, and nematodes. These experimental examples are intended to illustrate, not limit, the scope of the claimed invention.

Identification of Common Virulence Factors Required for *Pseudomonas aeruginosa* Pathogenicity in Plants and Animals To identify multi-host virulence factors, we first searched for bacterial pathogens capable of eliciting disease in both plant and animal pathogenesis models. A variety of *P. aeruginosa* isolates were screened using an *Arabidopsis thaliana* leaf pathogenesis infiltration system. Isolates which elicited disease symptoms in Arabidopsis were then tested for pathogenicity in a mouse full-thickness skin burn model and a nematode feeding assay.

Specifically, we first screened a collection of *P. aeruginosa* strains which included 30 human clinical isolates, 20 soil isolates, and 25 plant isolates (obtained from the University of California at Berkeley, Department of Plant Pathology). Each of these isolates was independently injected into the leaves of four different Arabidopsis ecotypes (land races or wild accessions) to determine whether the isolate was a plant pathogen. Several Arabidopsis ecotypes were assayed to increase the likelihood of identifying a suitable pathogen because plant pathogens, including Arabidopsis pathogens, typically exhibit a high level of host cultivar or ecotype specificity. Multiple host assays were also carried out because *P. aeruginosa* strains exhibiting ecotype specificity were more likely to be bona fide plant pathogens (rather than artifactual pathogens, capable of infecting plants only in the artificial environment created in the laboratory).

Screening experiments using an Arabidopsis leaf pathogenesis infiltration system were performed as follows. *P. aeruginosa* strains were grown in Luria Broth (LB) medium at 37° C., washed twice in 10 mM $MgSO_4$, resuspended at an optical density of 600 [$OD_{600}$]=0.2 in 10 mM $MgSO_4$, diluted 1:100 (corresponding to a bacterial density of $10^3$ cfu/$cm^2$), and injected into leaves of six week old Arabidopsis plants. Plants were kept in a growth chamber during the course of the experiment at 28–30° C. and 90–100% relative humidity. Disease symptoms and growth were monitored daily for five days. Symptoms elicited five days post-injection were characterized as: "none," no symptoms; "weak," localized weak water-soaking and chlorosis (yellowing) of tissue circumscribing the injection site; "moderate," moderate water-soaking and chlorosis with the majority of tissue softened around the inoculation site; or "severe," severe soft-rotting of the entire inoculated leaf characterized by a water-soaked reaction zone and chlorosis circumscribing the injection site at 2–3 days post-injection. The soft-rot symptoms pervaded the leaf at 4–5 days post-injection. Leaf intercellular fluid containing bacteria was harvested at five days, and bacterial counts were determined according to standard methods (see, e.g., Dong et al. (1991) *Plant Cell* 3:61). Four different samples were taken using two leaf discs per sample. Three independent experiments gave similar results. Control plants inoculated with 10 mM $MgSO_4$ showed no symptoms during the course of the experiments. In other control experiments, none of the genetically characterized *P. aeruginosa* strains PAK, PAO1, or PO37 caused appreciable symptoms on any of the Arabidopsis ecotypes tested. These strains were found to be non-pathogenic in the ecotypes tested, but pathogenic in culture.

While the majority of the 75 *P. aeruginosa* strains which were screened caused no symptoms in Arabidopsis leaves, several strains elicited weak to moderate soft-rot symptoms characterized by chlorosis and water-soaking of the tissue circumscribing the injection site. Two strains, UCBPP-PA14 (a human clinical isolate) and UCBPP-PA29 (a plant isolate) caused severe soft-rot symptoms in some of the ecotypes tested, typical of a highly virulent plant bacterial pathogen. Table I shows the growth of *P. aeruginosa* UCBPP-PA14 and UCBPP-PA29 five days post infection, and disease symptoms elicited by these *P. aeruginosa* strains on different Arabidopsis ecotypes. In particular, strain UCBPP-PA14 caused severe soft-rotting in both the Llagostera (Ll) and Columbia (Col) Arabidopsis ecotypes, but caused no symptoms in ecotype Argentat (Ag) and only moderate symptoms in ecotype Bensheim (Be). Table I also illustrates that strain UCBPP-PA29 caused severe symptoms in Ll and weak symptoms in Col, but caused no symptoms in Ag or Be.

TABLE I

| Arabidopsis Ecotype | *P. aeruginosa* UCBPP-PA14 | | *P. aeruginosa* UCBPP-PA29 | |
|---|---|---|---|---|
| | cfu/$cm^2$ leaf area | Symptoms | cfu/$cm^2$ leaf area | Symptoms |
| Llagostera | $2.6 \times 10^7 \pm 2.0 \times 10^7$ | Severe | $2.7 \times 10^7 \pm 1.3 \times 10^7$ | Severe |
| Columbia | $9.0 \times 10^6 \pm 6.0 \times 10^6$ | Severe | $6.0 \times 10^5 \pm 3.0 \times 10^5$ | Weak |
| Argentat | $3.0 \times 10^5 \pm 1.4 \times 10^5$ | None | $1.5 \times 10^5 \pm 9.0 \times 10^4$ | None |
| Bensheim | $1.1 \times 10^6 \pm 4.9 \times 10^5$ | Moderate | $4.5 \times 10^5 \pm 2.0 \times 10^5$ | None |

Figure 1:
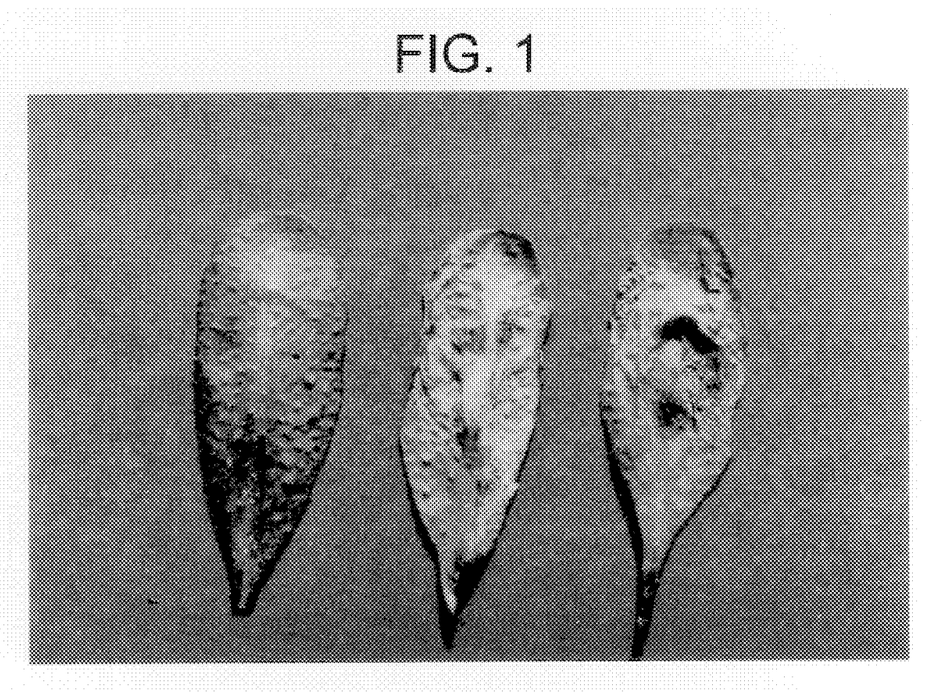
FIG. 1 is a color photograph showing the symptoms caused by *Pseudomonas syringae* and *Pseudomonas aeruginosa* on Arabidopsis (ecotype Llagostera (Ll)) leaves. Mock-inoculated (left); *Pseudomonas syringae* pv. maculicola strain ES4326 (center); *Pseudomonas aeruginosa* strains UCBPP-PA14 (right).

As shown in FIG. 1, the severe symptoms elicited by UCBPP-PA14 (far right) were characterized by a water-soaked reaction zone and chlorosis, resulting in complete maceration and collapse of the leaf 4 to 5 days post-infection (compare with control far left). These symptoms were essentially indistinguishable from the symptoms elicited by the highly virulent Arabidopsis pathogen *Pseudomonas syringae* pv. maculicola strain ES4326 (pictured in center).

Figure 2A:
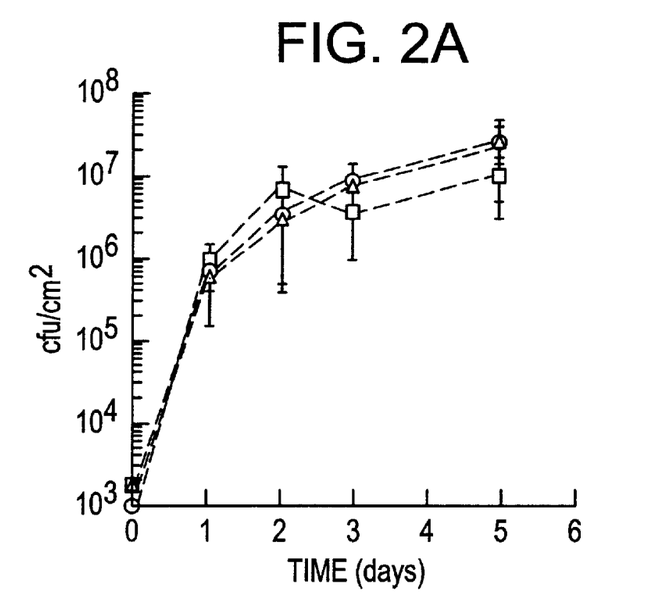
FIG. 2A is a graph showing the growth of *Pseudomonas syringae* pv. maculicola strain ES4326 (open squares), *Pseudomonas aeruginosa* strain UCBPP-PA14 (open circles), and *Pseudomonas aeruginosa* strain UCBPP-PA29 (open triangles) in ecotype Llagostera.
Figure 2B:
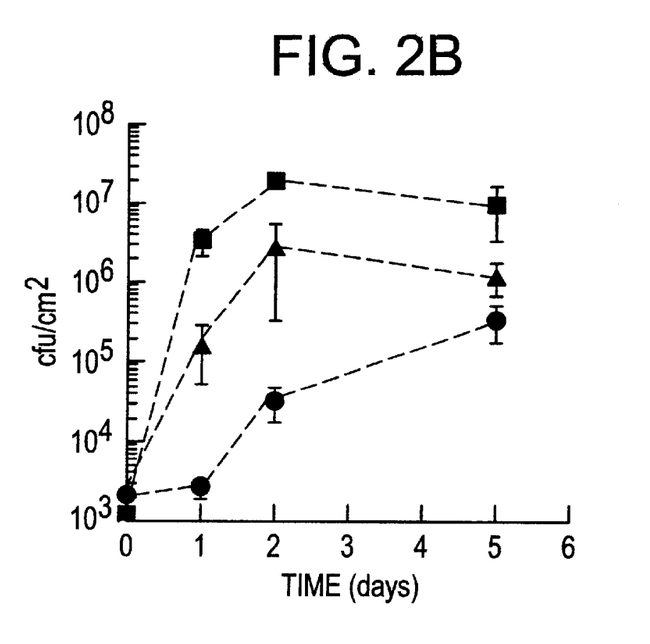
FIG. 2B is a graph showing the growth of *Pseudomonas aeruginosa* strain UCBPP-PA14 in three Arabidopsis ecotypes: Columbia (solid squares); Argentat (solid circles); and Bensheim (solid triangles).

To verify that the severity of disease symptoms was correlated with bacterial proliferation, growth of each of the strains UCBPP-PA14 and UCBPP-PA29 was measured over the course of several days in Arabidopsis leaves as described above. As shown in FIG. 2A, strains UCBPP-PA14 (open circles) and UCBPP-PA29 (open triangles) reached maximal bacterial density of approximately $10^7$ cells/cm$^2$ leaf area by five days in ecotype Ll, which corresponded to $10^4$-fold increases from the initial inocula. The growth profiles of these strains in Ll was similar to that of the virulent Arabidopsis pathogen *P. syringae* pv. maculicola strain ES4326 (FIG. 2A, open squares). Strain UCBPP-PA14 also proliferated $10^4$-fold in ecotype Col (FIG. 2B, solid squares; Table I). In contrast, strain UCBPP-PA14 increased only $10^3$- and $10^2$-fold in Be and Ag leaves, respectively (FIG. 2B, solid triangles and solid circles, respectively; Table I), and strain UCBPP-PA29 increased only $10^2$- to $6 \times 10^2$-fold in ecotypes Col, Ag, and Be (Table I). In each case, reduced bacterial counts in leaves reflected less severe symptom development. Accordingly, each of these *P. aeruginosa* a strains was similar to other phytopathogenic bacteria in its ability to cause disease in an ecotype-specific manner.

UCBPP-PA14 and UCBPP-PA29 isolates found to elicit disease symptoms in Arabidopsis were then tested in a mouse full-thickness skin burn injury assay. This involves 5% of the murine body surface area fashioned on an outstretched area of abdominal skin (Stevens et al. (1994) *J. of Burn Care and Rehabil.* 15:232). In this model, the damaged epidermis and dermis undergoes coagulation necrosis, but the underlying rectus abdomini (RA) muscles are not injured. In the absence of infection, all animals survive.

To carry out this pathogenesis assay, a *P. aeruginosa* inoculum is injected intradermally into the midline crease of the burn eschar. The bacteria proliferate in the burn wound, and some strains may invade the normal underlying RA muscles. Highly pathogenic strains can also invade the vasculature. The number of bacteria found in the RA muscles underlying and adjacent to the burn after 24 hours gives a quantitative measure of local invasiveness, and mortality indicates both local and systemic invasiveness.

Mouse full-thickness skin burn studies were performed as follows. Six week old male CD-1 mice (Charles River Animal Farms) weighing between 25 and 35 grams were used in all experiments, following an animal burn model (Stevens et al., supra). Mice were injected with ~$5 \times 10^3$ cells. No viable bacterial cells were retrieved from the underlying RA muscle immediately after bacterial injection or in animals who received a sham injury in other studies. In mortality studies, immediately following the burn, mice were injected with $10^2$ cells, and the number of animals which died of sepsis was monitored each day for ten days. Two groups of control animals consisting of (i) mice burned but not injected and (ii) mice injected with heat-killed UCBPP-PA14 resulted in 0% mortality.

Data shown in Table II (below) illustrate the proliferation of *P. aeruginosa* strains in a mouse full-thickness skin burn model. Table II indicates that strains UCBPP-PA14 and UCBPP-PA29 proliferated and invaded the RA muscles comparably to the well-characterized *P. aeruginosa* human isolates PO37, PAK, and PAO1. All strains reached titers ranging from $1.8 \times 10^8$ to $3.6 \times 10^8$ cfu per gram tissue in RA muscle biopsies taken directly beneath the burn and infection site (Table II). Furthermore, all strains reached titers ranging from $4.0 \times 10^7$ to $8.2 \times 10^7$ cfu per gram tissue in RA muscle biopsies taken adjacent to the burn. In addition, tissue samples processed for routine histology revealed that strain UCBPP-PA14 invaded the muscle to the same degree as strain PO37.

TABLE II

| *P. aeruginosa* Strain | Mean titer ± S.D. in biopsies underneath burn | Mean titer ± S.D. in biopsies adjacent to burn |
| --- | --- | --- |
| UCBPP-PA14 | $20.0 \times 10^7 \pm 9.0 \times 10^7$ | $6.0 \times 10^7 \pm 2.1 \times 10^7$ |
| UCBPP-PA29 | $36.0 \times 10^7 \pm 10.0 \times 10^7$ | $8.2 \times 10^7 \pm 2.0 \times 10^7$ |
| PO37 | $30.0 \times 10^7 \pm 11.0 \times 10^7$ | $5.8 \times 10^7 \pm 1.0 \times 10^7$ |
| PAK | $18.0 \times 10^7 \pm 9.1 \times 10^7$ | $6.0 \times 10^7 \pm 1.2 \times 10^7$ |
| PAO1 | $31.0 \times 10^7 \pm 10.0 \times 10^7$ | $4.0 \times 10^7 \pm 1.8 \times 10^7$ |

The virulence of strains UCBPP-PA14 and UCBPP-PA29 in comparison to PO37 was also assessed by conducting mortality studies in the mouse full-thickness skin burn model as described above. Strains UCBPP-PA14, UCBPP-PA29, and PO37 caused 77% (17/22), 6% (1/16), and 22% (2/9) mortality, respectively, by the tenth day post-burn and infection (Table III). Additional experiments showed strains PAO1 and PAK caused significantly less mortality in this model than UCBPP-PA14.

Strain UCBPP-PA14 was then selected for additional studies because it was infectious in both plant and animal pathogenicity models in which the outcome of pathogenesis could be quantitated, and because the level of virulence in these models was comparable to known plant and animal pathogens. Specifically, we sought to determine whether there were common virulence determinants in strain UCBPP-PA14 required for pathogenicity in both hosts. Our strategy was to use a marker exchange procedure to generate UCBPP-PA14 mutants carrying insertion mutations in four different genes, two known to be virulence determinants for *P. aeruginosa* in animal hosts, one known to be a virulence determinant for phytopathogenic bacteria in plant hosts, and one known to be a virulence determinant for several animal bacterial pathogens in animal hosts. The two animal virulence genes of *P. aeruginosa* were plcs and toxA encoding the exported proteins phospholipase C and exotoxin A, respectively (Ohman et al. (1980) *Infect. Immun.* 28: 899; Ostroff et al. (1987) *J. Bacteriol.* 169: 4597). Exotoxin A ribosylates G proteins, and phospholipase C preferentially degrades phospholipid of eukaryotic cells (Iglewski et al. (1975) *Proc. Natl. Acad. Sci.* 72:2284; Berka et al. (1982) *J. Bacteriol.* 152:239). The plant pathogen virulence determinant was gacA, identified as a global regulator of excreted anti-fungal factors in the non-pathogenic soil bacterium *P. fluorescens* (Laville et al. (1992) *Proc. Nat. Acad. Sci.* 89:1562; Gaffney et al. (1994) *Mol. Plant-Microbe Interact.* 7:455). In the phytopathogens *P. syringae* pv. syringae and *P. cichorrii*, gacA appears to serve as a transcriptional regulator of genes that encode extracellular products involved in pathogenicity (Rich et al. (1994) *J. Bacteriol.* 176:7468). The other animal virulence determinant, degp (also known as htrA), has been identified as a stress-response protease which is responsible for degrading incorrectly folded periplasmic proteins in Brucella and Salmonella (Elzer et al. (1994) *Infection and Immunity* 62: 4135; Johnson et al. (1991) *Mol. Microbiol.* 5: 410).

The UCBPP-PA14 homologues of plcs and toxA were identified in a genomic cosmid library of strain UCBPP-PA14 using cloned DNA fragments corresponding to the plcS and toxA genes of *P. aeruginosa* strain PAK as hybridization probes. A genomic library of strain UCBPP-PA14 was prepared according to standard methods in the cosmid cloning vector pJSR1, which was itself constructed by ligating a 1.6 kb BglII fragment containing the bacteriophage lambda cos site from pHC79 (see, e.g., Hohn et al. (1980) Gene 11: 291) into the BGlII site of pRR54 (see, e.g., Roberts et al. (1990) *J. Bacteriol.* 172: 6204). A 1.7 kb BamH1 fragment isolated from plasmid pMS150 containing the toxA gene (see, e.g. Lory et al. (1983) *Gene* 22:95) and a 3.0 kb BamH1PstI fragment isolated from plasmid pSL2 (see, e.g., Lory et al. (1988) *J. Bacteriol.* 170:714) containing the plcs gene were used to probe the UCBPP-PA14 genomic library in pJSR1.

The UCBPP-PA14 homologue of gacA was identified in the same cosmid library using a PCR-amplified product corresponding to a conserved region of the *P. fluorescens* gacA gene according to standard methods. The oligonucleotides 5'-GCTAGTAGTCGATGACC-3' (SEQ ID NO:1) and 5'-GCTGGCATCAACCATGC-3' (SEQ ID NO:2) were designed on the basis of the sequence of the gacA gene (Laville et al. (1992) *Proc. Natl. Acad. Sci.* 89:1562) and used to amplify a 625 base-pair product containing the gacA gene of *Psaudomonas fluorescens*, which in turn was used to probe the UCBPP-PA14 genomic library in pJSR1 described above. The UCBPP-PA14 homologue of the degP gene was identified in the UCBPP-PA14 cosmid library using the degP gene of *Pseudomonas syringae* pv. maculicola as a probe.

All four genes were subcloned and mutagenized by the insertion of a cassette encoding gentamicin resistance using standard methods.

In addition, a 6 kb BamHI fragment isolated from the cosmid clone containing the plcS gene of strain UCBPP-PA14 was subcloned from a pJSR1-derived cosmid into the BamHI site of pBR322. The resulting clone, pLGR101, was mutagenized by insertion of a gentamicin-encoding DNA cassette into the XhoI site of the plcs gene to construct pLGR201. The gentamicin-resistance gene cassette is a 1.8 kb BamHI fragment from plasmid pH1JI (see, e.g., Rubin (1987) *Plasmid* 18, 84). A 1.6 kb BamHI fragment containing the toxA gene was subcloned from a pJSR1-derived cosmid into pBR322 to construct pLGR102 and subsequently mutated by introducing the gentamicin cassette into the BglII site of the toxA gene to construct plasmid pLGR202. And a 2.5 kb HindIII-EcoRI fragment containing the *P. aeruginosa* strain UCBPP-PA14 gacA gene was subcloned from a pJSR1-derived cosmid into pBR322 to construct pLGR103. The presumptive gacA gene was partially sequenced to confirm that the UCBPP-PA14 gacA had been cloned. pLGR103 was mutagenized by inserting the gentamicin cassette into the SalI site of gacA to construct the plasmid pLGR203. A 1.6 Pst I fragment containing part of the degP gene was subcloned from pPY201 a derivative of the cosmid clone pH126 of the strain UCBPP-PA14 into the PstI site of pUC19 to construct PNAS. A 1.6 kb SalI fragment containing the gentamicin cassette was inserted into the XhoI site of the degP gene in pNAS to construct pNASGm. Next, a 3.2 kb SphI/XhoI fragment was isolated from the pNASGm vector and subcloned into the SphI/XhoI sites of pCVD442 to construct pPY206, which contained the mutated degP gene.

The mutated genes were transferred to the UCBPP-PA14 genome using standard marker exchange techniques, and the structures of the resulting marker exchange mutations were verified by DNA blot analysis. Thus, plasmids pLGR201, pLGR202, pLGR203, and pPY206 were used for gene replacement of the plcs, toxA, gacA, and degP genes respectively, by the method described in Rahme et al. (1991) *J. Bacteriol.* 170:575, using gentamicin at 30 mg/mL to screen for the double crossover events and carbenicillin at 300 mg/mL to screen for the loss of the vector. None of these four mutations had any detectable effect on the growth of the bacteria compared to wild-type in either rich or minimal media.

Figure 2C:
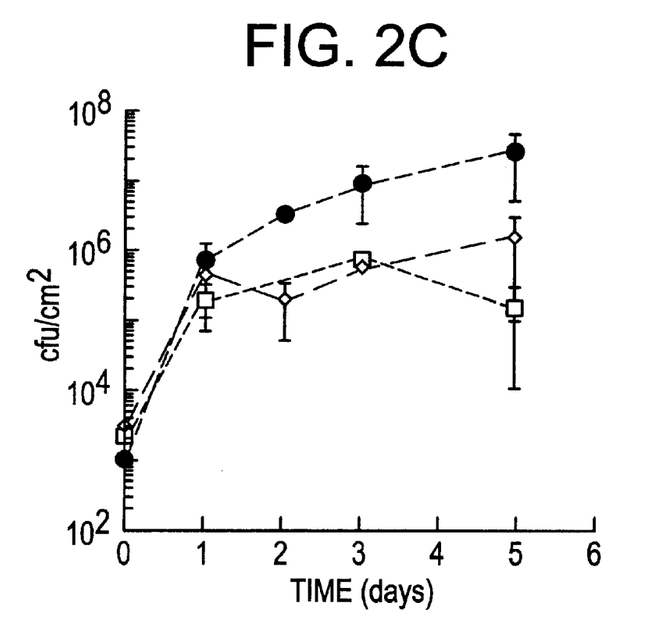
FIG. 2C is a graph showing the growth of *Pseudomonas aeruginosa* strain UCBPP-PA14 (solid circles) and isogenic plcs (open squares), and toxA (open diamonds) mutants.
Figure 2D:
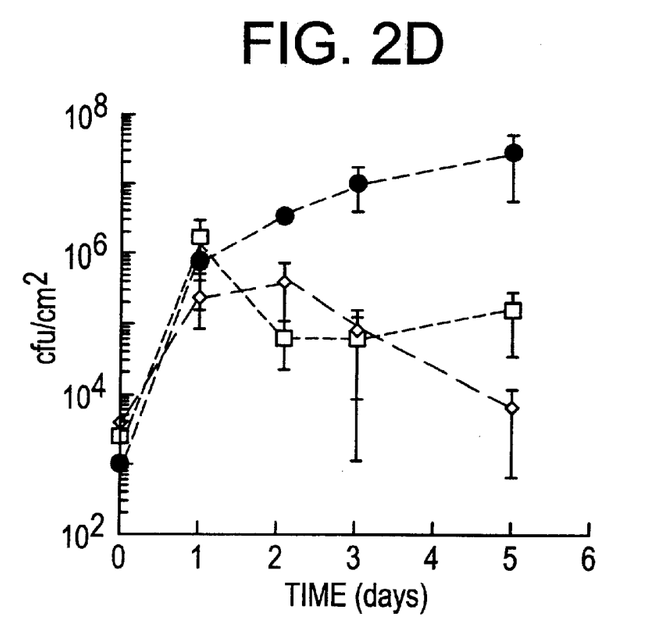
FIG. 2D is a graph showing the growth of *Pseudomonas aeruginosa* strain UCBPP-PA14 (solid circles), isogenic gacA (open diamonds), and degP (open squares) mutants in ecotype Llagostera. Bacterial counts in Arabidopsis leaves were performed as described herein. Means of four samples ± SD are shown. Three independent experiments gave similar results. Incubation conditions for the plants were identical to the experiments presented in Table I, infra.

The effects of the plcs, toxA, gacA, and degP mutations on the pathogenicity of UCBPP-PA14 in the Arabidopsis model were tested by infiltrating the mutant strains into Arabidopsis ecotype L1. Unlike wild-type UCBPP-PA14, none of the mutants caused maceration or collapse of the leaf. Specifically, the isogenic toxA mutant caused attenuated soft-rot and chlorosis symptoms without the accompanying maceration of the affected tissue characteristic of UCBPP-PA14. The plcs, gacA, and degp mutants elicited even weaker symptoms, causing only chlorosis. Consistent with the attenuated symptoms, growth of the toxA, plcS, gacA, and degP mutants after 5 days was approximately $10$-fold, $10^2$-fold, $5\times10^3$-fold, and $10^2$-fold less, respectively, than the growth of the wild type (FIGS. 2C and 2D).

The growth and symptoms of the three mutants tested (plcS, toxA, and gacA) were fully restored to wild-type levels in plants when these mutants were complemented with the corresponding wild-type genes carried on a plasmid. This was accomplished by subcloning a 6 kb BamH1 fragment from the cosmid clone pB85 of the genomic library containing the plcSR operon of strain UCBPP-PA14 into the BamHI site of plasmid pRR54 to construct pLGR301. Plasmid pLGR301 was then used for the genetic complementation studies of the plcS mutant. A 2.4 kb EcoRI/EcoRV fragment isolated from plasmid pMS150 containing the toxA gene of the strain PAK, was subcloned into the EcoRI/EcoRV sites of plasmid pBR322 to construct pLGR106. From pLGR106 a SphI/PstI fragment containing toxA was cloned into the SphI/PstI sites of pRR54 to construct pLRG206. A 1.2 kb HindIII/XhoI fragment containing the gacA gene was isolated from cosmid clone pH106 and subcloned into the HindIII/SalI sites of plasmid pRR54 to construct pLGR204. Plasmids pLRG206 and pLGR204 were then used for genetic complementation studies of the toxA and gacA mutants.

Table III shows lethality studies corresponding to these three mutant *P. aeruginosa* strains in a mouse full-thickness skin burn model. In such lethality studies, mice that were burned and infected with either plcS or toxA mutants exhibited significantly lower mortality (40% with both mutants) compared to infection with the wild-type strain (77%). The gacA and degP mutants caused no mortality (Table III). The differences in mortality rates between the mutants and wild-type was statistically significant at the 95% or greater confidence level. Statistical significance for mortality data was determined by using the chi-square test with Yates' correction. Groups were considered statistically significant at $P \leq 0.05$. All the mutants achieved statistical significance (plcS and toxA, $P=0.05$; gacA, $P=0.00005$).

TABLE III

| *P. aeruginosa* Strain | Mortality ratio of mice at 10 days following burn and infection |
|---|---|
| UCBPP-PA14 | 17/22 |
| UCBPP-PA14 plcs | 6/15 |
| UCBPP-PA14 toxA | 6/15 |
| UCBPP-PA14 gacA | 0/10 |
| UCBPP-PA14 degp | 0/11 |

TABLE III-continued

| P. aeruginosa Strain | Mortality ratio of mice at 10 days following burn and infection |
|---|---|
| UCBPP-PA29 | 1/16 |
| PO37 | 4/9 |

The above results demonstrate that plCs, toxA, gacA, and degP are involved in both plant and animal pathogenesis and indicate a part of the pathogen's machinery required for disease development is common or shared in animal and plant hosts. One of the shared virulence factors, gacA, is active at the regulatory level, demonstrating that mechanisms for regulation of virulence factors are conserved between plant and animal pathogens. The plcs and toxA gene products are specific virulence determinants which presumably attack the membranes and inhibit protein synthesis in both plant and animal cells, respectively.

To extend these results to a third host system, the pathogenicity of P. aeruginosa UCBPP-PA14 was measured in a nematode feeding assay. The feeding assay was set up as follows. First, 5 μl of an overnight culture of P. aeruginosa UCBPP-PA14, or an isogenic strain of P. aeruginosa UCBPP-PA14 carrying a degP or gacA mutation, was inoculated onto the center of an NGM agar plate and cultured for 24 hours at 37° C. After several hours of cooling at room temperature, the plates were seeded with eight Caenorhabditis elegans L4-stage worms. Plates were subsequently incubated in the dark at 25° C., and deceased worms were scored every 6 hours. A worm is considered dead when it is non-motile, no longer displays any pharyngeal pumping action, and no longer exhibits defecation behavior.

Figure 3:
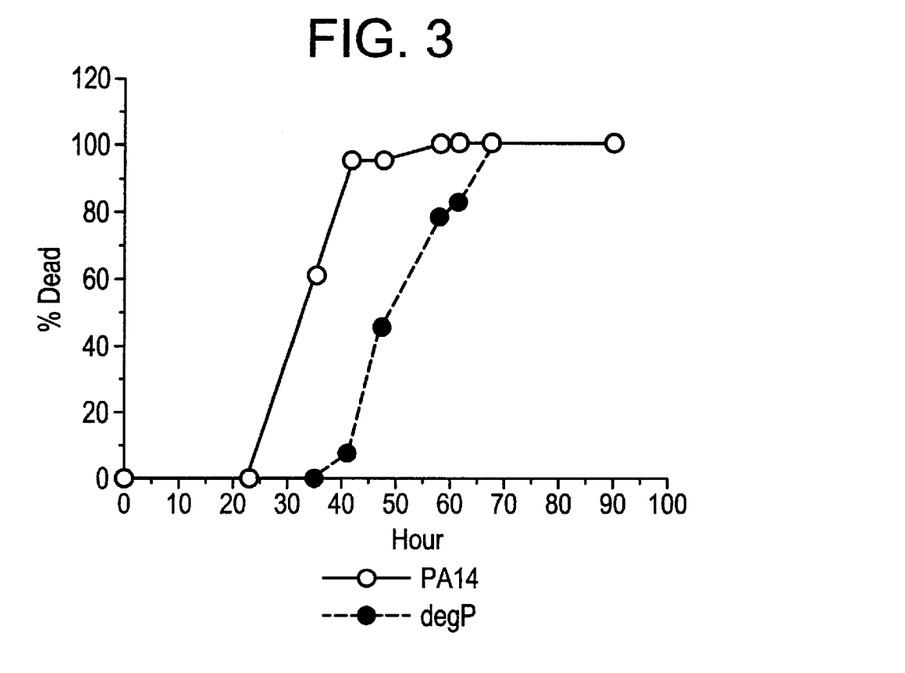
FIG. 3 is a graph showing a comparison of *Caenorhabditis elegans* lethality growing on wild-type *Pseudomonas aeruginosa* strain UCBPP-PA14 and on an isogenic degP mutant.
Figure 4:
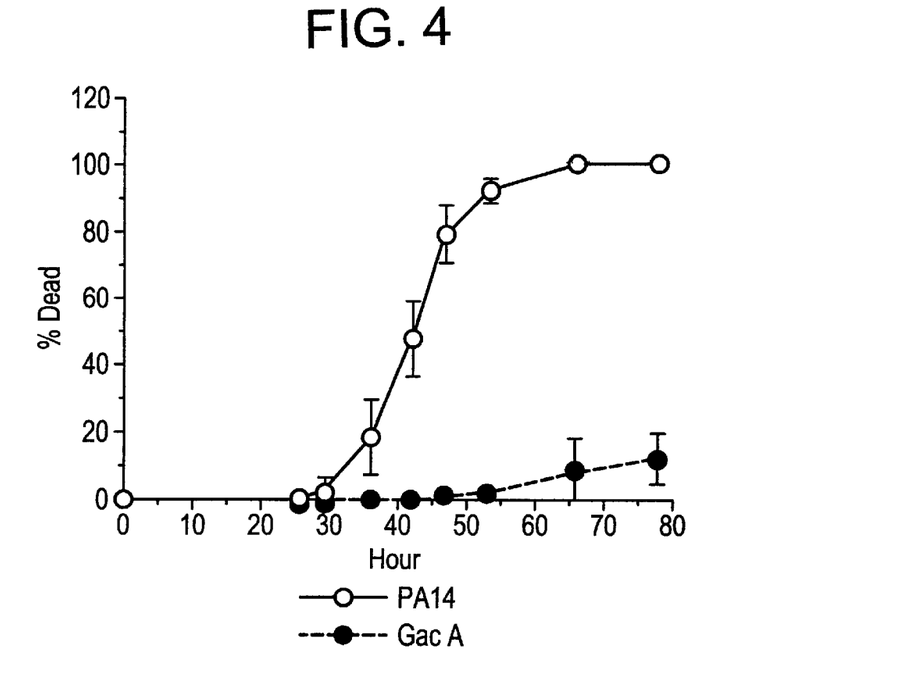
FIG. 4 is a graph showing a comparison of *Caenorhabditis elegans* lethality growing on wild-type *Pseudomonas aeruginosa* strain UCBPP-PA14 and on an isogenic gacA mutant.

FIGS. 3 and 4 show the results of the nematode feeding lethality assay using wild-type UCBPP-PA14 and its degP and gacA isogenic mutants, respectively. The results depicted in both FIG. 3 and FIG. 4 show that P. aeruginosa UCBPP-PA14 kills C. elegans. The results also show that isogenic mutants of P. aeruginosa UCBPP-PA14 carrying insertions which functionally disabled either the degP or gacA gene were significantly reduced in virulence in both the nematode and mouse full-thickness skin burn assay (FIGS. 3 and 4; Table III). The gacA gene is known to be a virulence determinant for P. syringae in plant hosts, and degP is known to be a virulence factor for both P. syringae and Salmonella typhimurium. As is discussed below, we have used these screening methods for identifying several mutants that exhibit reduced pathogenicity in nematodes and Arabidopsis; three of the mutants we isolated were found to be less pathogenic in mice.

The multi-host animal/plant pathogen system described herein has several practical ramifications. For example, these results indicate the molecular basis of pathogenesis is remarkably similar in plants and animals. Thus, as described below, the multi-host pathogen system can be used for the identification and study of new virulence factors. In particular, the entire P. aeruginosa genome can be scanned for pathogenicity-related genes by testing individually mutagenized P. aeruginosa in different host organisms, e.g., using the Arabidopsis or nematode assays described herein. Genes identified in this manner can then be tested in the mouse full-thickness skin burn model. This system also facilitates the elucidation of the molecular basis of host specificity of bacterial pathogens. Virulence factors identified using this model system provide targets for the development of a new generation of chemical therapies for both clinical and agricultural microbial diseases.

Screening Systems For Identifying Common Virulence Genes

Based on the results described above showing that a set of P. aeruginosa virulence factors are involved in pathogenicity in three diverse hosts and that these common virulence determinants define fundamental features of bacterial pathogenicity which are host independent, we have developed a method for identifying virulence determinants important for pathogenicity in plants and animals. The screen utilizes a multi-host animal/plant pathogen (e.g., P. aeruginosa UCBPP-PA14) and exploits the ability to readily screen thousands of randomly generated microbial mutants in virtually any host organism. Useful eukaryotic host organisms include, without limitation, nematodes (e.g., Caenorhabditis elegans), plants (e.g., a seed or leaf from Arabidopsis), yeast or other fungi, fish (e.g., zebrafish), flies (e.g., Drosophila melanogaster), mice, and the like. In general, a microbial pathogen is mutated according to standard methods known in the art and then subsequently evaluated for its ability to induce disease in the host organism. Mutagenized pathogens found to have diminished pathogenicity or which are rendered non-pathogenic are useful in the method of the invention. Such mutant pathogens are then used for identifying host-dependent or host-independent virulence factors responsible for pathogenicity according to methods known in the art.

The following is a working example of a virulence factor nematode screening system which utilizes the human clinical isolate P. aeruginosa UCBPP-PA14 found to be infectious in three different models: a mouse skin full-thickness burn model, a C. elegans nematode feeding model, and an Arabidopsis thaliana leaf infiltration model. The advantage of using a nematode as a host for studying a human or plant pathogen such as Pseudomonas is the relative simplicity of identifying non-pathogenic Pseudomonas mutants in the nematode. For example, a C. elegans screen consists of putting two L4 stage worms on a lawn of a P. aeruginosa mutant and looking for surviving worms after 5 days. A pathogen such as P. aeruginosa UCBPP-PA14 is mutated according to any standard procedure, e.g., standard in vivo or in vitro insertional mutagenesis methods (see, e.g., Kleckner et al. (1977) J. Mol. Biol. 116:125). other methods are also available, e.g., chemical mutagenesis. By the fifth day, very few or no live worms can be found in the plate seeded with wild-type, pathogenic bacteria, whereas on a plate with E. coli or a non-pathogenic mutant, hundreds or thousands of live progeny of the initial two hermaphrodite worms are present. Thus, worms growing in the presence of mutated P. aeruginosa is an indication that a gene responsible for pathogenicity has been inactivated. The positions of an inactivating mutations are mapped, leading to the cloning and identification of the mutated virulence factor (e.g., by nucleotide sequencing).

To identify genes involved in pathogenicity, we generated mutants of P. aeruginosa UCBPP-PA14 using standard techniques of transposon mutagenesis (see, e.g. Manoil et al. (1985) Proc. Natl. Acad. Sci. 82:8129; Taylor et al. (1989) J. Bacteriol. 171:1870); over 8000 mutants were generated. The pathogenicity of 1900 of these mutants was then assessed using the C. elegans feeding assay described above. As shown in Table IV, we isolated 8 UCBPP-PA14 mutants that exhibited attenuated pathogenicity in C. elegans.

In addition, we also examined the pathogenicity of another collection of mutants generated by transposon mutagenesis in a lettuce leaf pathogenesis assay using standard methods (see, e.g., Cho et al. (1975) Phytopathology 65:425). Using this assay, we isolated 2900 UCBPP- PA14 mutants with attenuated pathogenicity on lettuce leaves. These mutants were subsequently tested in the Arabidopsis leaf pathogenesis assay according to the methods described herein. As shown in Table IV, we isolated 12 UCBPP-PA14 mutants that exhibited attenuated pathogenicity in Arabidopsis.

TABLE IV

|  | Arabidopsis thaliana | C. elegans |
|---|---|---|
| No. of mutants tested | 2900 | 1900 |
| No. of attenuated mutants | 12 | 8 |

One UCBPP-PA14 mutant identified in the Arabidopsis infiltration assay was then tested for pathogenicity in both the C. elegans feeding assay and the mouse full-thickness skin burn assay. We found that this UCBPP-PA14 mutant was less pathogenic in both systems when compared to the wild-type UCBPP-PA14 strain. Furthermore, we also tested two mutants identified in the Arabidopsis bioassay for pathogenicity in the mouse full-thickness burn assay. These mutants were also found to be less pathogenic in mice when compared to the wild-type UCBPP-PA14 strain. Together these results provide further evidence for the existence of common virulence factors for pathogenicity in plants and animals.

The results described above demonstrate that pathogenic interactions occur between *P. aeruginosa* UCBPP-PA14 and *C. elegans*. Strain UCBPP-PA14 kills *C. elegans*. UCBPP-PA14 is also infectious in an *Arabidopsis thaliana* leaf infiltration assay (FIGS. 1 and 2; Table I) and in a mouse full-thickness skin burn model (Tables II and III). Furthermore, we have demonstrated that null mutations in UCBPP-PA14 degP and gacA genes significantly decrease pathogenesis in all three models. Thus, we have provided the first evidence for the existence of common virulence factors for pathogenicity in plants and animals. Such virulence factors make possible the isolation of compounds that interfere with virulence factor function (e.g., through direct reduction of pathogenicity or enhancement of a host response), and also make possible the identification of these compounds in simple experimental systems (e.g., Caenorhabditis).

Screening Systems for Identifying Therapeutics or Plant Protectants

As discussed above, our experimental results demonstrate that a set of *P. aeruginosa* virulence factors are involved in pathogenicity in three diverse hosts and that these common virulence determinants define fundamental features of bacterial pathogenicity which are host independent. Based on this discovery we have developed a screening procedure for identifying therapeutic compounds (e.g., anti-pathogenicity pharmaceuticals) which can be used to inhibit pathogens capable of independently infecting either an animal (e.g., a human patient) or a plant (e.g., a commercial crop plant). In general, the method involves screening any number of compounds for therapeutically- or agriculturally-active agents by employing the multi-host animal/plant pathogen (e.g., *P. aeruginosa* UCBPP-PA14) system(s) described herein. Based on our demonstration that there are common virulence factors for pathogenicity in plants, mice, and nematodes, it will be readily understood that a compound which interferes with the function of such a virulence factor in a nematode also provides an effective therapeutic agent in a mammal (e.g., a human patient) or a plant. Whereas most antibiotics currently in use in medicine or agriculture are either bactericidal or bacteriostatic, thus favoring strains or mutants resistant to them, the compounds identified in the screening procedures described herein (e.g., the nematode system) do not kill the bacteria but instead render them non-pathogenic. Moreover, since the screening procedures of the invention are performed in vivo, it is also unlikely that the identified compounds will be highly toxic to a eukaryotic host organism.

Accordingly, the methods of the invention simplify the evaluation, identification, and development of active agents such as drugs and plant protectants for the treatment of pathogenic diseases, including diseases caused by bacteria, fungi, viruses, annelids, nematodes, platyhelminthes, and protozoans. In general, the screening methods of the invention provide a facile means for selecting natural product extracts or compounds of interest from a large population which are further evaluated and condensed to a few active and selective materials. Constituents of this pool are then purified and evaluated in the methods of the invention to determine their anti-pathogenic activity.

Below we describe screening methods for evaluating the efficacy of a compound as an anti-pathogenic agent. These examples are intended to illustrate, not limit, the scope of the claimed invention.

Test Extracts and Compounds

In general, novel anti-pathogenic drugs or plant protectants are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have anti-pathogenic activity, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogenous extracts are known in the art. If desired, compounds shown to be useful agents for the treatment of pathogenicity are chemically modified according to methods known in the art.

There now follow examples of high-throughput systems useful for evaluating the efficacy of a molecule or compound in promoting resistance to a pathogen or inhibiting a pathogen. These examples are provided to illustrate, not limit, the invention.

Nematode Bioassay System

To enable mass screening of large quantities of natural products, extracts, or compounds in an efficient and systematic fashion, *Caenorhabditis elegans* L4 hermaphrodite larvae are cultured in wells of a microtiter plate, facilitating the semiautomation of manipulations and full automation of data collection. As is discussed above, we have discovered that *P. aeruginosa* a UCBPP-PA14 infects and kills *C. elegans*, whereas *P. aeruginosa* a UCBPP-PA14 carrying a mutagenized virulence gene is non-pathogenic. If a pathogen has diminished, pathogenicity then L4 worms live, develop into adult hermaphrodites, and produce thousands of live progeny. Accordingly, if *C. elegans* is incubated with the pathogen, the worms will die, unless a compound is present to reduce *P. aeruginosa* a pathogenicity. The presence of such live progeny is easily detected using a variety of methods, including visual screening with standard microscopes.

To evaluate the ability of a test compound or extract to promote a host's resistance to a pathogen or to repress pathogenicity of a pathogen, a test compound or extract is inoculated at an appropriate dosage into NGM agar seeded with an appropriate amount of an overnight culture of a pathogen, e.g., *P. aeruginosa* UCBPP-PA14. If desired, various concentrations of the test compound or extract can be inoculated to assess dosage effect on both the host and the pathogen. Control wells are inoculated with non-pathogenic bacteria (negative control) or a pathogen in the absence of a test compound or extract (positive control). Plates are then incubated 24 hours at 37° C. to facilitate the growth of the pathogen. Microtiter dishes are subsequently cooled to 25° C., and two *C. elegans* L4 hermaphrodite larva are added to the plate and incubated at 25° C., the upper limit for normal physiological integrity of *C. elegans*. At an appropriate time interval, e.g., 4 to 5 days, wells are examined for surviving progeny, e.g., by monitoring motion of worms using a motion detector.

Comparative studies between treated and control larvae are used to determine the relative efficacy of the test molecule or compound in promoting the host's resistance to the pathogen or inhibiting the virulence of the pathogen. A test compound which effectively stimulates, boosts, enhances, increases, or promotes the host's resistance to the pathogen or which inhibits, inactivates, suppresses, represses, or controls pathogenicity of the pathogen and does not adversely affect the normal physiology, reproduction, or development of the worms is considered useful in the invention.

Plant Bioassay System

To enable mass screening of large quantities of natural products, extracts, or compounds in an efficient and systematic fashion, host plants (e.g., seeds, seedlings, plantlets, embryos, mature plants, or leaves) are cultured in wells of a microtiter plate or any other suitable container, facilitating the semiautomation of manipulations and full automation of data collection. Particular examples of suitable plant hosts useful in this bioassay include, without limitation, petunia, tomato, potato, tobacco, Arabidopsis, soybean, corn, wheat, rye, rice, barley, or any other plant of commercial or agricultural significance. Methods for culturing plants are known in the art (see, e.g., Vasil, I. K., *Cell Culture* and *Somatic Cell Genetics of Plants* Vol I, II, III, Laboratory Procedures and Their Applications, Academic Press, New York, 1984; Dixon R. A., *Plant Cell Culture—A Practical Approach*, IRL Press, Oxford University, 1985). As is discussed above, we have discovered that *P. aeruginosa* a UCBPP-PA14 infects and kills *Arabidopsis thaliana*, whereas *P. aeruginosa* UCBPP-PA14 carrying a mutagenized virulence gene is non-pathogenic. Accordingly, if a pathogen has diminished pathogenicity, the plant will not develop symptoms or, alternatively, will develop attenuated symptoms relative to control plants. If *Arabidopsis thaliana* plants are incubated with the pathogen, the plants will die or have a variety of disease symptoms (e.g., chlorosis or soft-rot), unless a compound is present to reduce *P. aeruginosa* pathogenicity. The presence of such live seedlings and their associated disease symptoms is easily detected using a variety of methods, including visual screening.

To evaluate the ability of a test compound or extract to promote a host's (e.g., *Arabidopsis thaliana*) resistance to a pathogen or to repress pathogenicity of a pathogen, a test compound or extract is inoculated at an appropriate dosage into a tissue culture media (e.g., a solidified agar-based medium). In addition, if desired, the host plant can be pretreated with the candidate plant protectant or anti-pathogen compound by any conventional means, e.g., a seedling or plantlet can be sprayed with a solution containing the test compound. Host plants are assayed using any standard pathogenesis screening system, e.g., the Arabidopsis and lettuce leaf infiltration assays described above, or by standard vacuum infiltration techniques. For example, host seedlings are vacuum infiltrated with the pathogen according to standard methods. After vacuum infiltration seedlings are cultured according to methods known in the art (e.g., methods for culturing Arabidopsis are found in *Methods in Arabidopsis Research*, Koncz, C., Chua, N.-H., Schell, J., eds., World Scientific Publishing Co. Pte. Ltd., Singapore, 1992). If desired, various concentrations of the test compound or extract can be inoculated to assess dosage effect on both the host and the pathogen. Control seedlings are infiltrated with non-pathogenic bacteria (negative control) or a pathogen in the absence of a test compound or extract (positive control). At an appropriate time interval, e.g., 3 to 5 days, seedlings are examined for disease symptoms. Comparative studies between treated and control seedlings are used to determine the relative efficacy of the test molecule or compound in promoting the host's resistance to the pathogen or inhibiting the virulence of the pathogen. A test compound which effectively stimulates, boosts, enhances, increases, or promotes the host's resistance to the pathogen or which inhibits, inactivates, suppresses, represses, or controls pathogenicity of the pathogen and does not adversely affect the normal physiology, reproduction, or development of the seedlings is considered useful in the invention.

Use

The methods of the invention provide a simple means for identifying microbial virulence factors and compounds capable of either inhibiting pathogenicity or enhancing an organism's resistance capabilities to a pathogen. Accordingly, a chemical entity discovered to have medicinal or agricultural value using the methods described herein are useful as either drugs, plant protectants, or as information for structural modification of existing anti-pathogenic compounds, e.g., by rational drug design. Such methods are useful for screening compounds having an effect on a variety of pathogens including, but not limited to, bacteria, viruses, fungi, annelids, nematodes, platyhelminthes, and protozoans. Examples of pathogenic bacteria include, without limitation, Aerobacter, Aeromonas, Acinetobacter, Agrobacterium, Bacillus, Bacteroides, Bartonella, Bortella, Brucella, Calymmatobacterium, Campylobacter, Citrobacter, Clostridium, Cornyebacterium, Enterobacter, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio, and Yersinia.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections which provide continuous, sustained levels of the drug in the patient. Treatment of human patients or other animals will be carried out using a therapeutically effective amount of an anti-pathogenic agent in a physiologically-acceptable carrier. Suitable carriers and their formulation are described, for example, in Remington's *Pharmaceutical Sciences* by E. W. Martin. The amount of the anti-pathogenic agent to be administered varies depending upon the manner of administration, the age and body weight of the patient, and with the type of disease and extensiveness of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation. For example, for systemic administration a compound is administered typically in the range of 0.1 ng–10 g/kg body weight.

For agricultural uses, the compositions or agents identified using the methods disclosed herein may be used as chemicals applied as sprays or dusts on the foliage of plants. Typically, such agents are to be administered on the surface of the plant in advance of the pathogen in order to prevent infection. Seeds, bulbs, roots, tubers, and corms are also treated to prevent pathogenic attack after planting by controlling pathogens carried on them or existing in the soil at the planting site. Soil to be planted with vegetables, ornamentals, shrubs, or trees can also be treated with chemical fumigants for control of a variety of microbial pathogens. Treatment is preferably done several days or weeks before planting. The chemicals can be applied by either a mechanized route, e.g., a tractor or with hand applications. In addition, chemicals identified using the methods of the assay can be used as disinfectants.

All publications and patents mentioned in this specification are herein incorporated by reference to the same extent as if each individual publication or patent was specifically and individually indicated to be incorporated by reference.

From the foregoing description, one skilled in the art can easily ascertain the essential characteristics of this invention, can make various changes and modifications of the invention to adapt it to various usages and conditions. Thus, other embodiments are also within the claims.

Deposit

*Pseudomonas aeruginosa* strain UBCPP-PA14 has been deposited with the American Type Culture Collection on Mar. 22, 1995, and bears the accession number ATCC No. 55664. Applicants acknowledge their responsibility to replace this strain should it loose viability before the end of the term of a patent issued hereon, and their responsibility to notify the American Type Culture Collection of the issuance of such a patent, at which time the deposit will be made available to the public. Prior to that time the deposit will be made available to the Commissioner of Patents under terms of CFR §1.14 and 35 USC §112.

What is claimed is:

1. A method for identifying a pathogenic virulence factor, comprising
    (a) identifying a pathogen which is capable of infecting at least two different eukaryotic organisms, said two different eukaryotic organisms being chosen from (i) an animal and a plant or (ii) a vertebrate and an invertebrate;
    (b) generating a mutant of said pathogen;
    (c) exposing each of said organisms to said mutated pathogen;
    (d) determining whether said mutated pathogen is capable of causing disease in each of said organisms, a reduction of disease in both of said organisms relative to that caused by said wild-type pathogen indicating a mutation in said pathogenic virulence factor; and
    (e) using said mutation as a marker for identifying said pathogenic virulence factor.

2. A method for mutating a pathogenic virulence factor, comprising
    (a) identifying a pathogen which is capable of infecting at least two different eukaryotic organisms, said two different eukaryotic organisms being chosen from (i) an animal and a plant or (ii) a vertebrate and an invertebrate;
    (b) generating a mutant of said pathogen;
    (c) exposing each of said organisms to said mutated pathogen; and
    (d) determining whether said mutated pathogen in capable of causing disease in each of said organisms, a reduction of disease in both of said organisms relative to that caused by said wild-type pathogen indicating a mutation in said pathogenic virulence factor.

3. A method of reducing the virulence of a pathogen, comprising
    (a) identifying a pathogen which is capable of infecting at least two different eukaryotic organisms, said two different eukaryotic organisms being chosen from (i) an animal and a plant or (ii) a vertebrate and an invertebrate;
    (b) generating a mutant of said pathogen;
    (c) exposing each of said organisms to said mutated pathogen; and
    (d) determining whether said mutated pathogen is capable of causing disease in each of said organisms, a reduction of disease in both of said organisms relative to that caused by said wild-type pathogen indicating a reduction in said pathogen virulence.

4. The method of claim 1, 2, or 3, wherein said animal is a vertebrate.

5. The method of claim 4, wherein said vertebrate is a rodent.

6. The method of claim 4, wherein said plant is a crucifer.

7. The method of claim 1, 2, or 3, wherein said animal is an invertebrate.

8. The method of claim 7, wherein said invertebrate is a nematode.

9. The method of claim 7, wherein said plant is a crucifer.

10. The method of claim 1, 2, or 3, wherein said vertebrate is a rodent.

11. The method of claim 1, 2, or 3, wherein said invertebrate is a nematode.

12. The method of claim 1, 2, or 3, wherein said pathogen is a bacterium.

* * * * *

UNITED STATES PATENT AND TRADEMARK OFFICE
CERTIFICATE OF CORRECTION

PATENT NO. : 6,461,854 B1
DATED : October 8, 2002
INVENTOR(S) : Ausubel et al.

It is certified that error appears in the above-identified patent and that said Letters Patent is hereby corrected as shown below:

Column 1,
Lines 31-32, replace "*Cornynebacterium*" with -- *Corynebacterium* --.

Column 8,
Line 54, replace "*cichorrii*" with -- *cichorii* --;
Line 57, replace "degp" with -- degP --; and
Line 63, replace "plcs" with -- plcS --.

Column 9,
Line 5, replace "BGlII" with -- BglII --;
Line 22, replace "*Psaudomonas*" with -- *Pseudomonas* --; and
Line 65, replace "plcs" with -- plcS --.

Column 10,
Line 6, replace "plcs" with -- plcS --;
Line 15, replace "plcs" with -- plcS --; and replace "degp" with -- degP --; and
Table III, replace "plcs" with -- plcS --; and replace "degp" with -- degP --.

Column 11,
Line 9, replace "plCs" with -- plcS --; and
Line 16, replace "plcs" with -- plcS --.

Column 19,
Line 41, replace "in" with -- is --.

Signed and Sealed this

Eighth Day of February, 2005

JON W. DUDAS
*Director of the United States Patent and Trademark Office*